(12) United States Patent
Glimsdale

(10) Patent No.: US 10,321,991 B2
(45) Date of Patent: Jun. 18, 2019

(54) COLLAPSIBLE VALVE HAVING PARAVALVULAR LEAK PROTECTION

(71) Applicant: St. Jude Medical, Cardiology Division, Inc., St. Paul, MN (US)

(72) Inventor: Mathias Charles Glimsdale, St. Michael, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 77 days.

(21) Appl. No.: 14/899,371

(22) PCT Filed: Jun. 13, 2014

(86) PCT No.: PCT/US2014/042336
§ 371 (c)(1),
(2) Date: Dec. 17, 2015

(87) PCT Pub. No.: WO2014/201807
PCT Pub. Date: Dec. 24, 2014

(65) Prior Publication Data
US 2016/0143732 A1    May 26, 2016

Related U.S. Application Data

(60) Provisional application No. 61/837,063, filed on Jun. 19, 2013.

(51) Int. Cl.
*A61F 2/24* (2006.01)

(52) U.S. Cl.
CPC .......... *A61F 2/2418* (2013.01); *A61F 2/2409* (2013.01); *A61F 2220/0075* (2013.01);
(Continued)

(58) Field of Classification Search
None
See application file for complete search history.

(56) References Cited

U.S. PATENT DOCUMENTS 3,657,744 A    4/1972   Ersek
4,275,469 A    6/1981   Gabbay
(Continued)

FOREIGN PATENT DOCUMENTS

DE    19857887 B4    5/2005
DE    10121210 B4    11/2005
(Continued)

OTHER PUBLICATIONS

International Search Report and Written Opinion for Application No. PCT/US2014/042336 dated Sep. 30, 2014.
(Continued)

*Primary Examiner* — Christopher D. Prone
*Assistant Examiner* — Tiffany P Shipmon
(74) *Attorney, Agent, or Firm* — Lerner, David, Littenberg, Krumholz & Mentlik, LLP

(57) ABSTRACT

A heart valve assembly (100) includes a heart valve (116), a self-expandable and collapsible stent (112), and a sealing member (114). The stent (112) includes an inflow end (120) and an outflow end (122), and surrounds and supports the heart valve (116). The sealing member (114) is connected to the inflow end (120) of the stent (112) and extends around a periphery of the stent (112). The sealing member (114) is connected to the inflow end (120) of the stent (112), overlaps a portion of the heart valve (116), and extends around an outer periphery of the stent (112).

14 Claims, 13 Drawing Sheets

(52) U.S. Cl.
CPC ............ *A61F 2230/0065* (2013.01); *A61F 2230/0069* (2013.01); *A61F 2240/001* (2013.01); *A61F 2250/0069* (2013.01); *A61F 2250/0096* (2013.01)

(56) References Cited

U.S. PATENT DOCUMENTS

| | | | |
|---|---|---|---|
| 4,423,730 A | 1/1984 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,817,126 A | 10/1998 | Imran |
| 5,843,167 A | 12/1998 | Dwyer et al. |
| 5,855,601 A | 1/1999 | Bessler et al. |
| 5,924,424 A | 7/1999 | Stevens et al. |
| 5,935,163 A | 8/1999 | Gabbay |
| 5,961,549 A | 10/1999 | Nguyen et al. |
| 5,968,068 A | 10/1999 | Dehdashtian et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,306,141 B1 | 10/2001 | Jervis |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |

(56) References Cited

U.S. PATENT DOCUMENTS

| | | |
|---|---|---|
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0074484 A1 | 4/2006 | Huber |
| 2006/0106415 A1 | 5/2006 | Gabbay |
| 2006/0122692 A1 | 6/2006 | Gilad et al. |
| 2006/0142848 A1 | 6/2006 | Gabbay |
| 2006/0149360 A1 | 7/2006 | Schwammenthal et al. |
| 2006/0161249 A1 | 7/2006 | Realyvasquez et al. |
| 2006/0167468 A1 | 7/2006 | Gabbay |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0038291 A1* | 2/2007 | Case .................. A61F 2/2418 623/1.16 |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0073391 A1 | 3/2007 | Bourang et al. |
| 2007/0088431 A1 | 4/2007 | Bourang et al. |
| 2007/0093890 A1 | 4/2007 | Eliasen et al. |
| 2007/0100435 A1 | 5/2007 | Case et al. |
| 2007/0112422 A1 | 5/2007 | Dehdashtian |
| 2007/0118210 A1 | 5/2007 | Pinchuk |
| 2007/0162100 A1 | 7/2007 | Gabbay |
| 2007/0167955 A1* | 7/2007 | Arnault De La Menardiere ........ A61F 2/954 606/108 |
| 2007/0168013 A1 | 7/2007 | Douglas |
| 2007/0203575 A1 | 8/2007 | Forster et al. |
| 2007/0213813 A1 | 9/2007 | Von Segesser et al. |
| 2007/0233228 A1 | 10/2007 | Eberhardt et al. |
| 2007/0239271 A1 | 10/2007 | Nguyen |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147182 A1 | 6/2008 | Righini et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0054975 A1 | 2/2009 | del Nido et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0224678 A1 | 9/2011 | Gabbay |
| 2011/0264206 A1 | 10/2011 | Tabor |
| 2012/0035722 A1 | 2/2012 | Tuval |
| 2012/0065728 A1* | 3/2012 | Gainor .................. A61F 2/2436 623/2.11 |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0018458 A1 | 1/2013 | Yohanan et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0277423 A1* | 9/2014 | Alkhatib ............... A61F 2/2418 623/2.38 |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1129744 A1 | 9/2001 |
| EP | 1157673 A2 | 11/2001 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |

(56) References Cited

FOREIGN PATENT DOCUMENTS

| WO | 9913801 | A1 | 3/1999 | |
|---|---|---|---|---|
| WO | 01028459 | A1 | 4/2001 | |
| WO | 0149213 | A2 | 7/2001 | |
| WO | 01054625 | A1 | 8/2001 | |
| WO | 01056500 | A2 | 8/2001 | |
| WO | 01076510 | A2 | 10/2001 | |
| WO | 0236048 | A1 | 5/2002 | |
| WO | 0247575 | A2 | 6/2002 | |
| WO | 03047468 | A1 | 6/2003 | |
| WO | 06073626 | A2 | 7/2006 | |
| WO | 07071436 | A2 | 6/2007 | |
| WO | 08070797 | A2 | 6/2008 | |
| WO | 10008548 | A2 | 1/2010 | |
| WO | 10008549 | A1 | 1/2010 | |
| WO | 10051025 | A1 | 5/2010 | |
| WO | 10087975 | A1 | 8/2010 | |
| WO | 10096176 | A1 | 8/2010 | |
| WO | 10098857 | A1 | 9/2010 | |
| WO | 2012048035 | A2 | 4/2012 | |
| WO | 2012178115 | A2 | 12/2012 | |
| WO | WO 2012178115 | A2 * | 12/2012 | ........... A61F 2/2418 |

OTHER PUBLICATIONS

Ruiz, Carlos, Overview of PRE-CE Mark Transcatheter Aortic Valve Technologies, Euro PCR, 2010.
Quaden, Rene et al.,Percutaneous aortic valve replacement: resection before implantation, 836-840, European J. of Cardio-thoracic Surgery, 27 (2005).
U.S. Appl. No. 29/375,243, filed Sep. 20, 2010.
U.S. Appl. No. 29/375,260, filed Sep. 20, 2010.
Knudsen, L.L., et al.Catheter-implanted prosthetic heart valves,The International Journal of Artificial Organs, vol. 16, No. 5 1993, pp. 253-262.
Moazami, Nader, et al.,Transluminal Aortic Valve Placement, ASAIO Journal, 1996; 42:M381-M385.
Andersen, Henning Rud, Transluminal Catheter Implanted Prosthetic Heart Valves, International Journal of Angiology 7:102-106 (1998).
Andersen, H. R., et al., Transluminal implantation of artificial heart valves, European Heart Journal (1992) 13, 704-708.
Zegdi, Rachid, MD, PhD et al., Is It Reasonable to Treat All Calcified Stenotic Aortic Valves With a Valved Stent?, 579-584, J. of the American College of Cardiology, vol. 51, No. 5, Feb. 5, 2008.
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets In Vitro by Q-Switched 2 μm Microsecond Laser Radiation. Journal of Cardiac Surgery, 30: 157-162. doi: 10.1111/jocs.12481.
Muñoz, Daniel Rodriguez, Carla Lázaro Rivera, and José Luis Zamorano Gómez. "Guidance of treatment of perivalvular prosthetic leaks." Current cardiology reports 16.1 (2014): 1-6.
Gössl, Mario, and Charanjit S. Rihal. "Percutaneous treatment of aortic and mitral valve paravalvular regurgitation." Current cardiology reports 15.8 (2013): 1-8.
Swiatkiewicz, Iwona, et al. "Percutaneous closure of mitral perivalvular leak." Kardiologia polska 67.7 (2009): 762.
De Cicco, Giuseppe, et al. "Aortic valve periprosthetic leakage: anatomic observations and surgical results." The Annals of thoracic surgery 79.5 (2005): 1480-1485.
Heat Advisor, "Heart repairs without surgery. Minimally invasive procedures aim to correct valve leakage", Sep. 2004, PubMed ID 15586429.
Transcatheter Umbrella Closure of Valvular and Paravalvular Leaks, Houlihan et al., Journal of the American College of Cardiology, vol. 20, No. 6, pp. 1371-1377, (1992).
Buellesfeld et al., Treatment of paravalvular leaks through inverventional techniques; Department of Cardiology, Ben University Hospital 2011.

\* cited by examiner

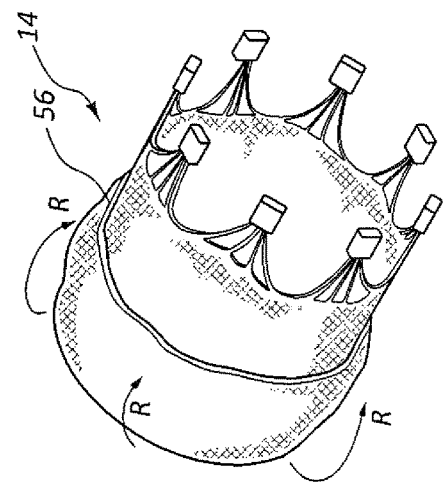
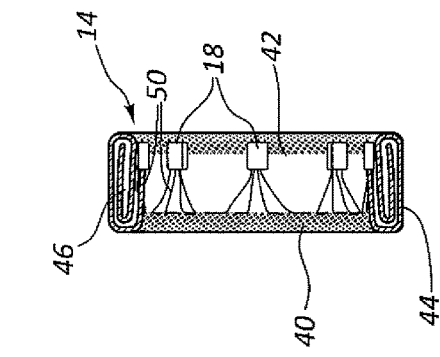
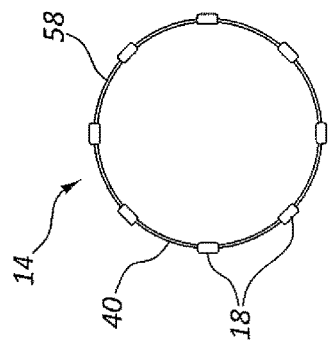
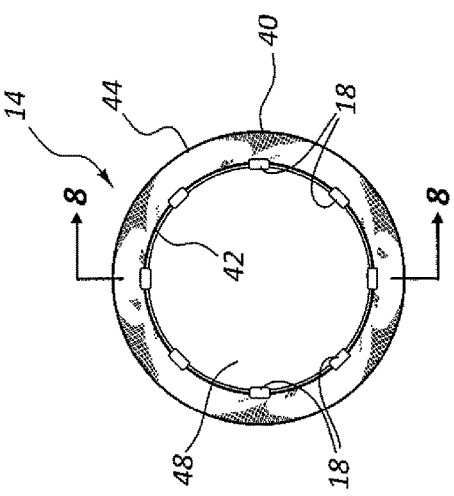
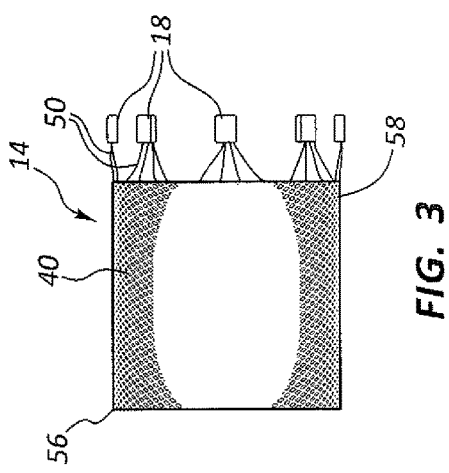
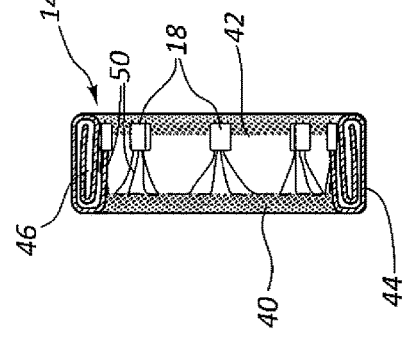

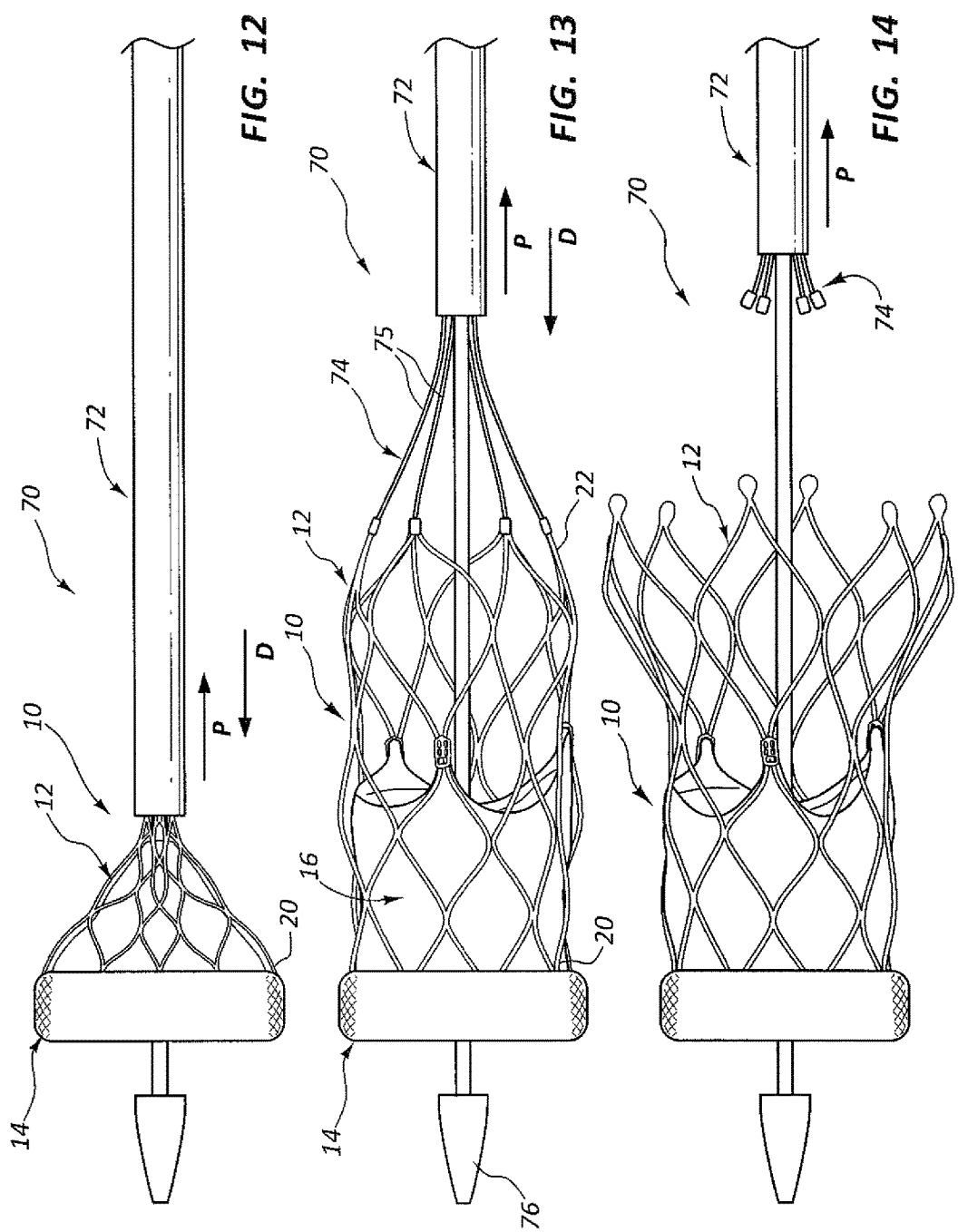

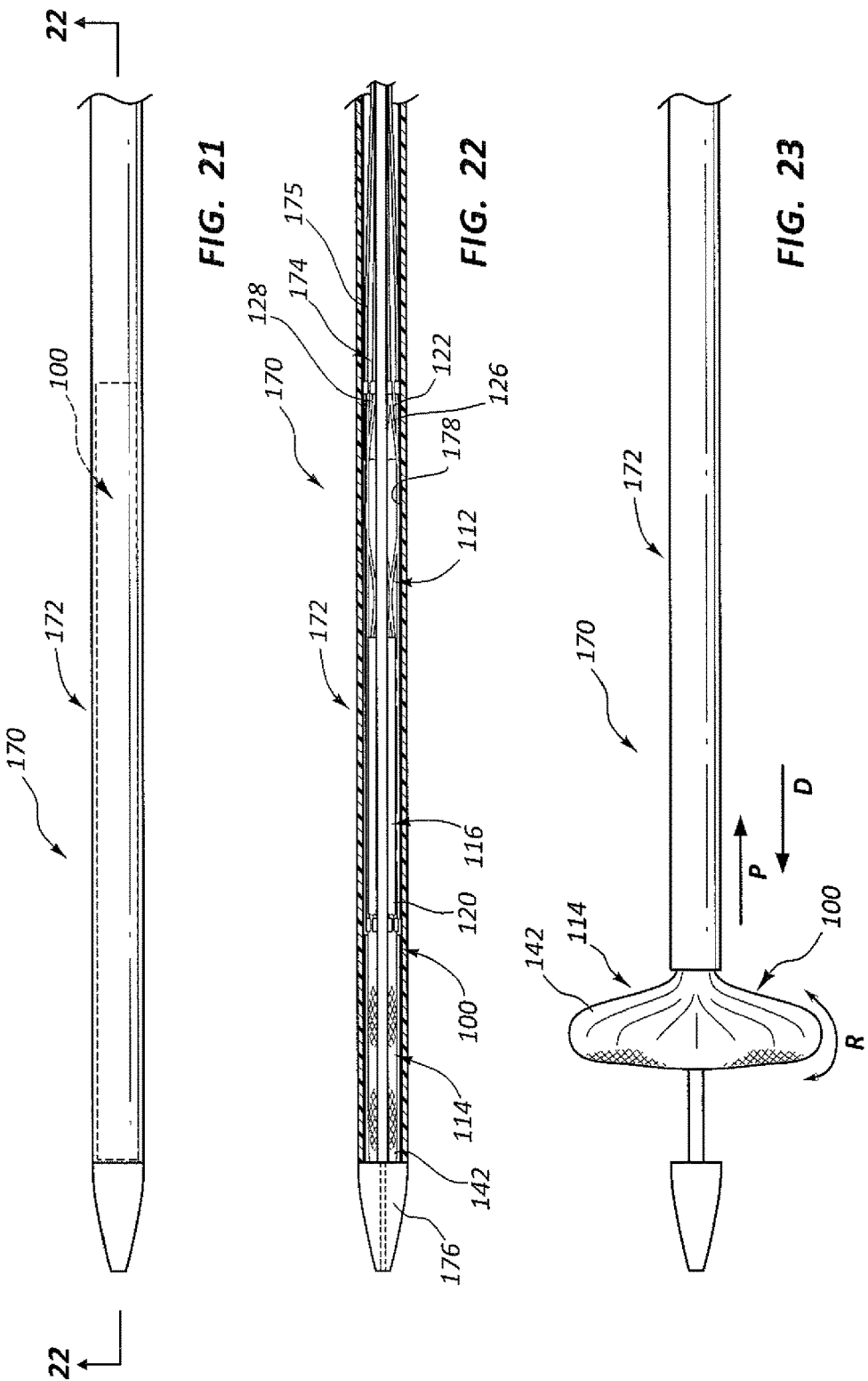

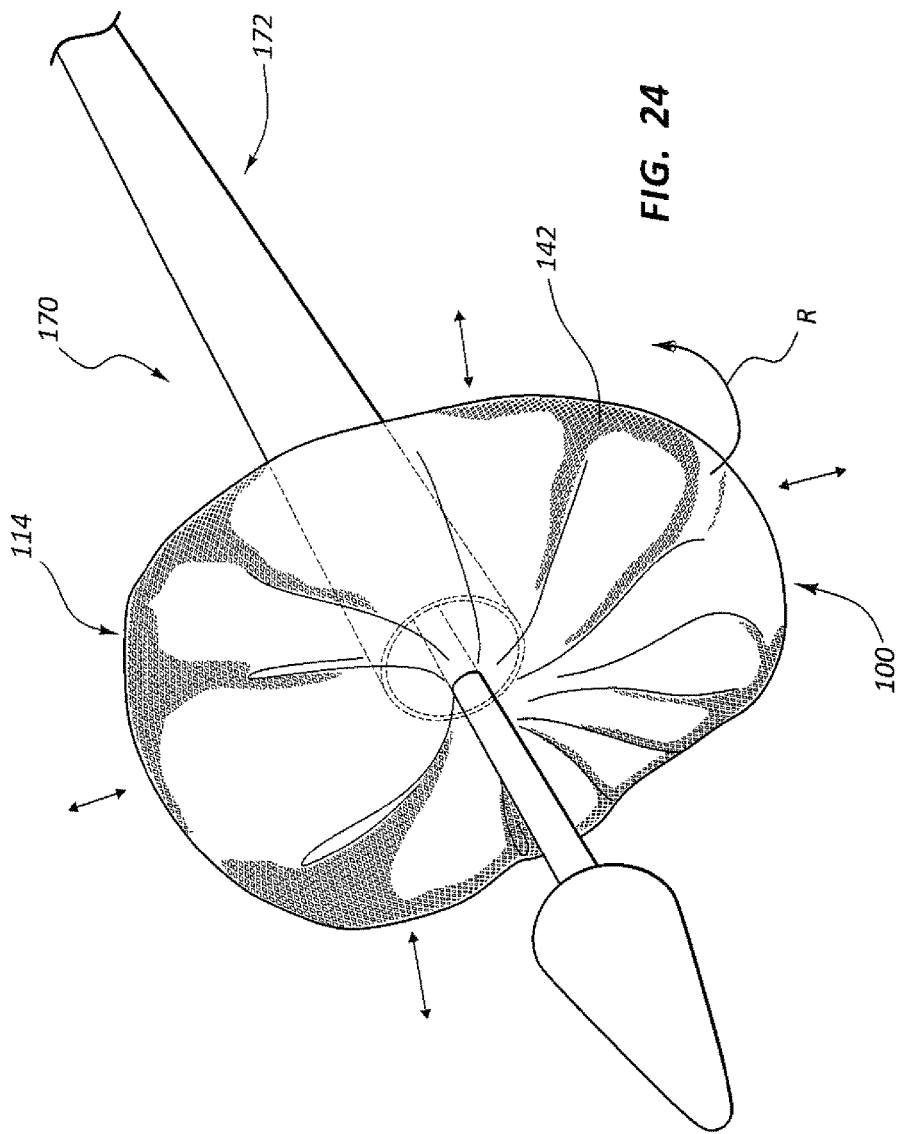

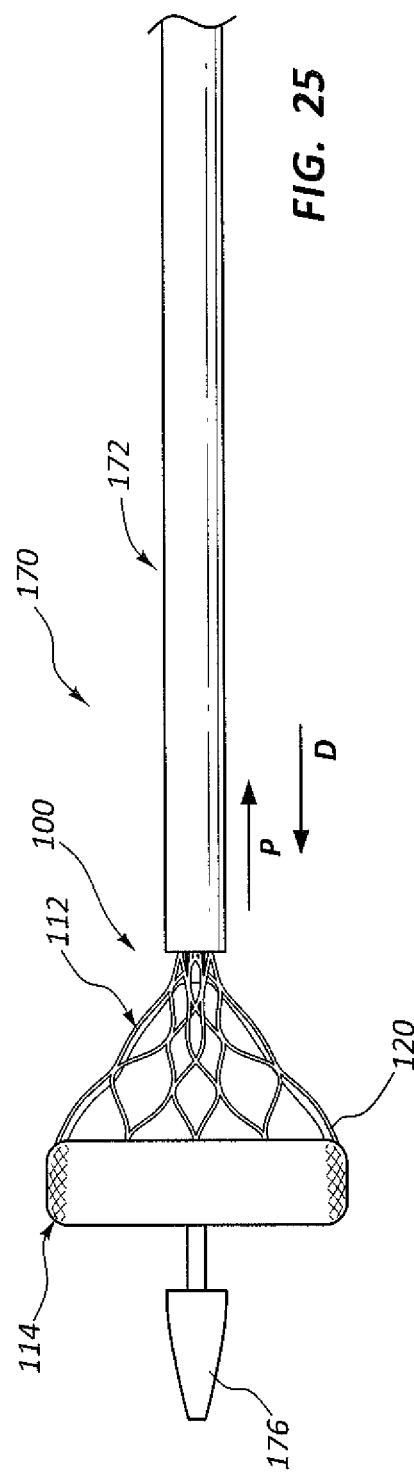

COLLAPSIBLE VALVE HAVING PARAVALVULAR LEAK PROTECTION

CROSS-REFERENCE TO RELATED APPLICATION

This application is a national phase entry under 35 U.S.C. § 371 of International Application No. PCT/US2014/042336, filed Jun. 13, 2014, which claims priority to U.S. Provisional Patent Application No. 61/837,063, filed Jun. 19, 2013, the disclosures of which are incorporated herein by reference.

TECHNICAL FIELD

The present disclosure relates to replacement heart valves, and more specifically relates to collapsible heart valves and associated sealing devices and methods.

BACKGROUND OF THE INVENTION

Prosthetic heart valves may be formed from biological materials such as harvested bovine valves or pericardial tissue. These valves are typically fitted within a stent, which may be inserted into the heart at the annulus of the compromised native valve to replace the native valve. To perform an insertion procedure using a minimally invasive transcatheter technique, it may be necessary to compress the stent to a reduced diameter for loading into a delivery device.

Paravalvular (or perivalvular) leak (PVL) is a relatively rare complication related to the replacement of native heart valves. PVL describes a condition of blood flowing between the implanted valve structure and the cardiac tissue rather than through the implanted valve structure as desired. While most PVLs are hemodynamically non-significant, significant leaks may be problematic and require further intervention.

SUMMARY OF THE INVENTION

A heart valve assembly in accordance with the present disclosure includes a heart valve, a self-expandable and collapsible stent, and a sealing member. The stent includes an inflow end and an outflow end, and surrounds and supports the heart valve. The sealing member is connected to the inflow end of the stent and extends around a periphery of the stent. The sealing member is connected to the inflow end of the stent, overlaps a portion of the heart valve, and extends around an outer periphery of the stent.

Another aspect of the present disclosure relates to a heart valve assembly that includes a heart valve, a self-expandable and collapsible stent, and a sealing member. The stent includes an inflow end and an outflow end, and surrounds and supports the heart valve. The sealing member includes a wire mesh having a hollow toroid shape with a central opening and an inward facing surface when in an expanded configuration. The sealing member is collapsible into an elongated configuration for delivery through a vessel. The stent extends into the central opening and is connected to the inward facing surface at a plurality of connection points when in the expanded configuration.

A further aspect of the present disclosure relates to a method of manufacturing a heart valve assembly. The method may include providing a stent and a sealing member that each have a self-expandable and collapsible construction. The stent includes an inflow end and an outflow end and is configured to support a heart valve internally. The method includes positioning the sealing member around an outer periphery of the stent at the inflow end and connecting the stent to the sealing member at a plurality of connection points.

Another method in accordance with the present disclosure relates to a method of deploying a heart valve assembly at an annulus. The method includes providing the valve assembly including a stent surrounding a valve member and a sealing member connected to the stent, and collapsing the valve assembly such that the sealing member and stent are in series.

The foregoing and other features, utilities, and advantages of the invention will be apparent from the following detailed description of the invention with reference to the accompanying drawings.

BRIEF DESCRIPTION OF THE DRAWINGS

FIG. 3 is a side view of a sealing member of the heart valve assembly of FIG. 1 in an unrolled position.

FIG. 4 is an end view of the sealing member of FIG. 3.

FIG. 5 is a perspective view of the sealing member of FIG. 3 in a partially rolled up position.

FIG. 6 is a side view of the sealing member of FIG. 5 in an expanded, fully rolled up position.

FIG. 7 is an end view of the sealing member of FIG. 6.

FIG. 8 is a cross-sectional view of the sealing member of FIG. 7 taken along cross-section indicators 8-8.

FIGS. 11-14 are a series of side views of the heart valve assembly and delivery system of FIG. 9 in various stages of being deployed.

FIG. 21 is a side view of the heart valve assembly of FIG. 16 located within a delivery system prior to deployment.

FIG. 22 is a cross-sectional view of the heart valve assembly and delivery system of FIG. 21 taken along cross-section indicators 22-22.

FIG. 23 is a side view of the heart valve assembly and delivery system of FIG. 21 in a first partially deployed position.

FIG. 24 is a perspective view of the heart valve assembly and delivery system of FIG. 23.

FIG. 25 is a side view of the heart valve assembly of FIG. 23 in a second partially deployed position.

DETAILED DESCRIPTION

The present disclosure is directed to implantable heart valve assemblies and support structures, sealing devices, and other features for use with heart valve assemblies. The systems and methods disclosed herein may have particular application to addressing paravalvular leak (PVL) conditions. The heart valve assembly may include a stent positionable at an annulus of a native heart valve (e.g., a native annulus). The stent may be a self-expandable and collapsible stent. A valve and an associated valve cuff may be mounted within the stent. The heart valve assembly may include a sealing member positioned circumferentially around an outer peripheral surface of the stent. The sealing member may at least partially fill openings or gaps between the native annulus and the outside of the stent and/or valve of the heart valve assembly.

The sealing members disclosed herein may comprise a wire mesh. The wire mesh may comprise a shape memory material. The wire mesh may be self-expandable from a compressed, collapsed position, which is maintained during delivery of the heart valve assembly through a vessel to an implantation site, to an expanded position for positioning within a native annulus at the implantation site. The stent may be directly connected to the sealing member. In one embodiment, distal free ends of the stent are connected to an interior surface of the sealing member. The stent may be connected to the sealing member using, for example, welding, a fastener (e.g., clip, bracket, sleeve, hypotube, marker band, suture, etc.), or a hook feature formed in either a portion of the stent or a portion of the sealing member.

The sealing member may have various configurations in the expanded position and in the unexpanded, collapsed position. The sealing member may include an elongate tubular shape when in the unexpanded, collapsed position. One end of the tubular shaped sealing member may be attached to a distal end of the stent. As the sealing member is deployed out of a carrier tube used to deliver the heart valve assembly to the implantation site, an opposite end of the tubular shaped sealing member rolls upon itself to create a toroid-shaped sealing member. A toroid shape is generally a donut-shaped object, such as an O-ring. A toroid-shaped object may have a hollow construction or may be solid.

In another example, the sealing member has a toroid shape when deployed and the stent is connected to the toroid-shaped sealing member along an interior, radially inward facing surface of the sealing member. The toroid-shaped sealing member is collapsible during delivery to the implantation site. The sealing member self-expands from the collapsed position into the toroid shape upon being deployed at the implantation site. The sealing member may invert or flip as part of expanding from the collapsed position to the deployed position. In this sealing member design, no rolling or unrolling of the sealing member is required as part of being deployed.

Figure 1:
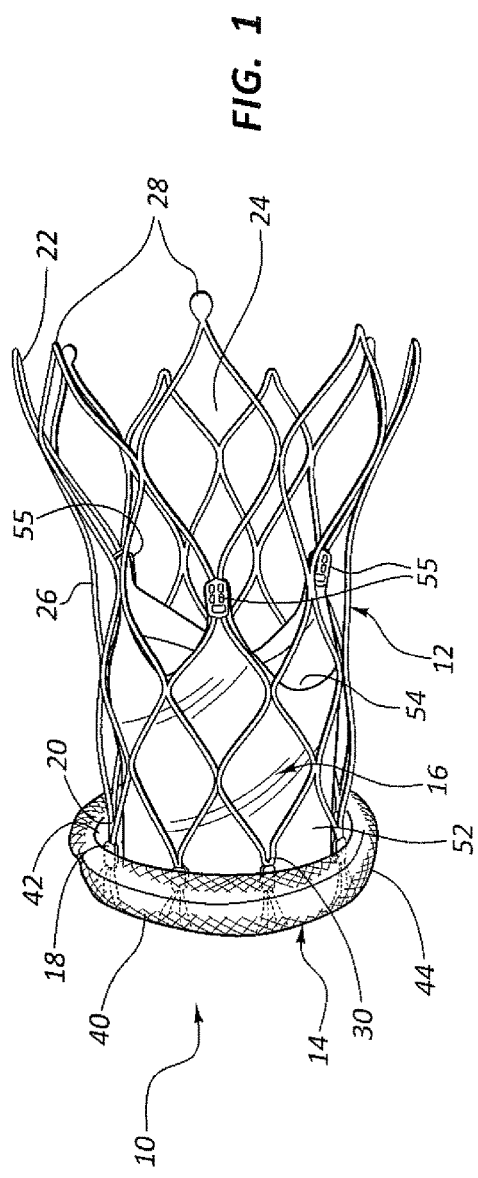
FIG. 1 is a perspective view of a heart valve assembly in accordance with the present disclosure.
Figure 2:
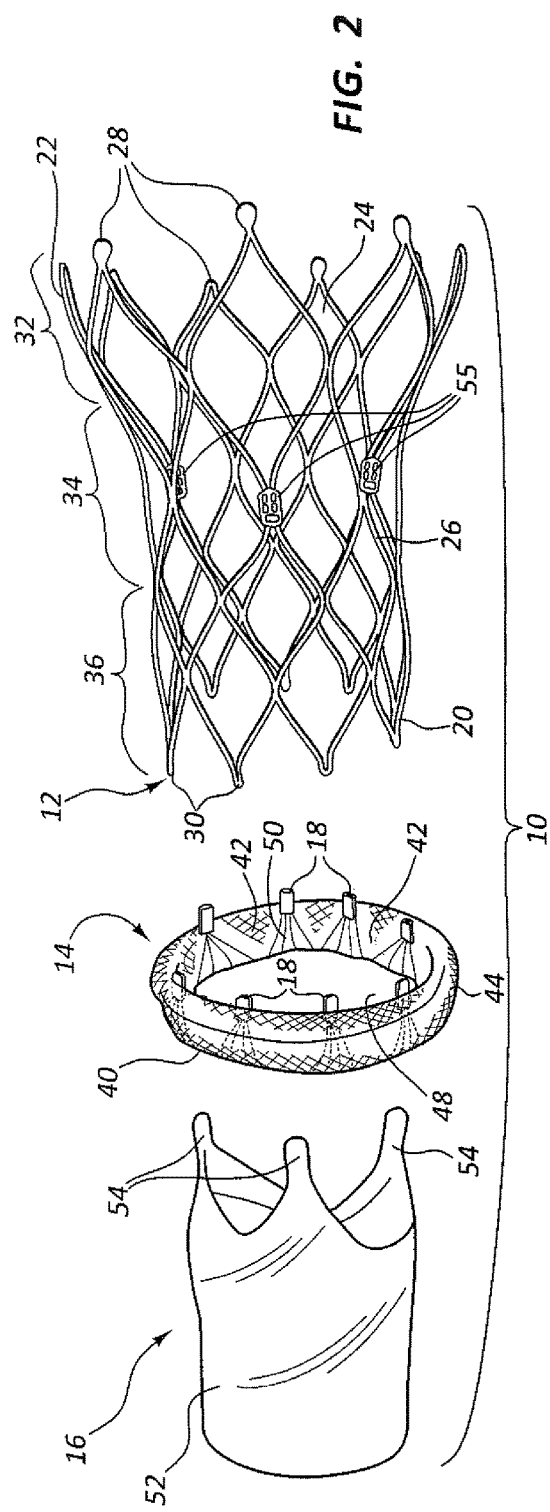
FIG. 2 is an exploded perspective view of the heart valve assembly of FIG. 1.

Referring now to FIGS. 1-14, and particularly FIGS. 1-2, heart valve assembly 10 is shown including stent 12, sealing member 14, and valve 16. Sealing member 14 may be used with a variety of different stents and valves to provide the sealing functions disclosed herein.

Valve 16 is positioned internally within stent 12. Stent 12 surrounds and internally supports valve 16. Sealing member 14 is positioned around an exterior, peripheral surface of stent 12. Sealing member 14 may provide an improved interface between heart valve assembly 10 and a native annulus at an implantation site (e.g., at a native valve site located at an outlet of a heart chamber). Sealing member 14 may be positioned at any desired location along a length of stent 12. In FIG. 1, sealing member 14 is positioned at or near a distal (e.g., inlet) end of stent 12. Sealing member 14 may be connected to free ends of the frame members that make up stent 12. Pairs of frame members may join together at the distal, inlet end of stent 12 to provide connection points 18 for connecting stent 12 to sealing member 14. Stent 12 is connected to sealing member 14 along an interior, radially inward facing surface of sealing member 14 when heart valve assembly 10 is in the deployed position of FIG. 1.

Stent 12 includes inflow and outflow end portions 20, 22 (also referred to as distal and proximal end portions, respectively), interior 24, and a plurality of frame members 26 (also referred to as struts), which form cells. Frame members 26 include free proximal ends 28 and free distal ends 30. Free proximal ends 28 may be coupled together in pairs and free distal ends 30 may be coupled together in pairs.

Stent 12 includes aortic section 32, sinus section 34, and annulus section 36 (see FIG. 2). Annulus section 36 is typically aligned radially with a native annulus at an implantation site. The native annulus may be defined by, for example, a portion of a native heart valve which has been damaged and/or at least partially removed and is being replaced by heart valve assembly 10. Aortic section 32 may be flared radially outward further than sinus and annulus sections 34, 36 when stent 12 is fully deployed. The additional radial expansion of aortic section 32 may provide improved anchoring of stent 12 within a vessel such as the aorta. At least some of free proximal ends 28 may include connection features for securing stent 12 to a delivery system used to move heart valve assembly 10 during delivery of heart valve assembly 10 and deploying heart valve assembly 10 at an implantation site (see FIG. 15).

Sealing member 14 includes wire mesh 40, interior surface 42 (e.g., radially inward facing surface), exterior surface 44 (e.g., radially outward facing surface), hollow interior 46 (see FIG. 8), and opening 48, which is sized to receive stent 12. Wire mesh 40 includes a plurality of wire members woven together into a braided arrangement. Sealing member 14 may include a single layer of wire mesh 40, or may include at least two layers of wire mesh 40. For example, sealing member 14 may include a double layer of wire mesh 40.

Individual wires, which include free ends 50 (see FIGS. 2, 3 and 5), may be separated out from the braided arrangement of each layer of wire mesh 40. Free ends 50 of a single layer or multiple layers may be grouped together to provide connection points 18 for connecting sealing member 14 to stent 12. In one example, about 3 to about 15 free ends 50 are grouped together to form a single connection point 18. Free ends 50 may be separated from the braided arrangement by combing out the individual wires, which may include inserting teeth of a comb structure into wire mesh 40 and pulling the comb structure axially along a length of wire mesh 40.

Each connection point 18 may include a fastener. The fasteners at connection points 18 may include, for example, welds, clips, sutures, or another type of direct connection between free ends 50 of the wire members of sealing member 14 and free distal ends 30 of frame members 26 of stent 12 (e.g., using twists, bends, loops, etc.). Connection points 18 may comprise materials that are visible under x-ray, and may be referred to as markers or marker bands.

In the embodiment depicted, stent 12 (and other stents disclosed herein) is connected to sealing member 14 with about 3 to about 15 connection points, and more particularly about 4 to about 8 connection points. The number of connection points 18 may be defined at least in part by the number of frame members 26 or pairs of frame members 26 of stent 12 and a mesh density of sealing member 14.

Wire mesh 40 of sealing member 14 (and other wire meshes disclosed herein) may have a wire density in the range of, for example, about 40 wires to about 200 wires, and more particularly in the range of about 75 wires to about 150 wires. While the term "wire" is used to describe the mesh and individual members of the mesh of the sealing member, other structures such as one or more filaments, threads or strands may be used. Wire mesh 40 may comprise a metal material or may comprise other materials such as, for example, polymer or fabric materials. Wire mesh 40 may comprise a shape memory material such as Nitinol.

Valve 16 shown in FIGS. 1-2 includes cuff 52 and a plurality of leaflets 54. Cuff 52 is usually connected to stent 12 using, for example, attachment stitching (not shown). Leaflets 54 may be connected to stent 12 using connectors 55. In the depicted embodiment, three leaflets 54 are shown, although more or less may be used depending on the desired function and location for valve 16. Sealing member 14 may overlap a portion of cuff 52 when heart valve assembly 10 is deployed in the position shown in FIG. 1.

Sealing member 14 may be automatically moveable between a first, collapsed orientation shown in FIGS. 3 and 4 and a second, expanded orientation shown in FIGS. 6-8. In the first orientation, sealing member 14 has an elongated tubular shape with distal and proximal ends 56, 58. Sealing member 14 in the first orientation may have a double layer of wire mesh 40 material having a plurality of braided individual wires. Free ends 50 of the individual wires are separated from the braided arrangement of wires in wire mesh 40 at proximal end 58. Free ends 50 are grouped together in bunches of about 3 to about 20 strands. The bunches of strands are spaced apart around a circumference of sealing member 14 at proximal end 58. The number of bunches of strands formed may equal the number of frame members 26 or pairs of frame members 26 at free distal end 30 of stent 12. In at least some embodiments, all free ends 50 of the individual wires of wire mesh 40 at proximal end 58 are separated out from the braided structure of wire mesh 40 and gathered into one of the bunches of strands. The number of strands in each bunch may be determined by dividing the total number of strands (e.g., 144 strands) by the number of attachment points to stent 12. Providing a substantially equal number of strands in each bunch may provide symmetry of forces in delivering, re-sheathing, and implanting sealing member 14 at the native annulus.

The bunches of strands may be held together by first applying a marker band around the bunch of strands at a predetermined distance away from distal end 56 when sealing member 14 is in the unrolled orientation of FIGS. 3 and 4. The marker band may be secured to the strands using, for example, welding or bonding. The excess length of the strands extending proximally beyond the marker band may be removed.

The bunches of strands are secured to free distal end 30 of stent 12 at connection points 18 (see FIG. 1). Connection points 18 may include the marker bands discussed above. The first orientation shown in FIG. 3 and may be a radially expanded, unrolled arrangement for sealing member 14. The unrolled arrangement shown in FIGS. 3 and 4 may be compressed radially inward to reduce a diameter of the tubular shape to provide a reduced profile for sealing member 14. The reduced diameter provides a smaller outer profile for purposes of delivery to a native annulus.

Free ends of individual wires at distal end 56 of sealing member 14, when in the orientation shown in FIGS. 3-4, may be held together in a braided arrangement for wire mesh 40. Distal end 56 may include a weld, crimp, fold or other feature that maintains the individual wires of wire mesh 40 held together in the braided arrangement. Distal end may be rolled up as discussed in further detail below related to the second orientation of sealing member 14 shown in FIGS. 6-8.

Figure 10:
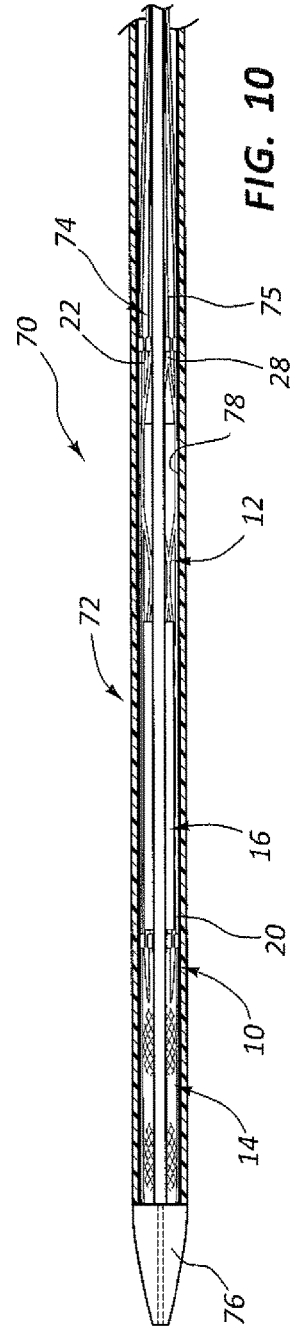
FIG. 10 is a cross-sectional view of the heart valve assembly and delivery system of FIG. 9 taken along cross-section indicators 10-10.

The first orientation depicted in FIG. 3 is maintained while sealing member 14 is positioned within carrier tube 72 (e.g., see FIG. 10). This first orientation is maintained upon application of an exterior applied constricting force (e.g., force imposed by positioning sealing member 14 within carrier tube 72). Upon gradual removal of an exterior applied force (e.g., removal of sealing member 14 from carrier tube 72), distal end 56 begins to roll upon itself or invert in a direction R, as shown in FIG. 5. Sealing member 14 may expand radially outward concurrently with rolling upon itself. As sealing member 14 continues to be freed from a constraining force (e.g., deployed out of carrier tube 72), distal end 56 continues to roll upon itself until sealing member 14 achieves the second orientation shown in FIGS. 6-8. The rolled up second orientation may include at least one complete roll, and typically includes at least one and a half to two rolls as shown in the cross-section of FIG. 8.

Figure 15:
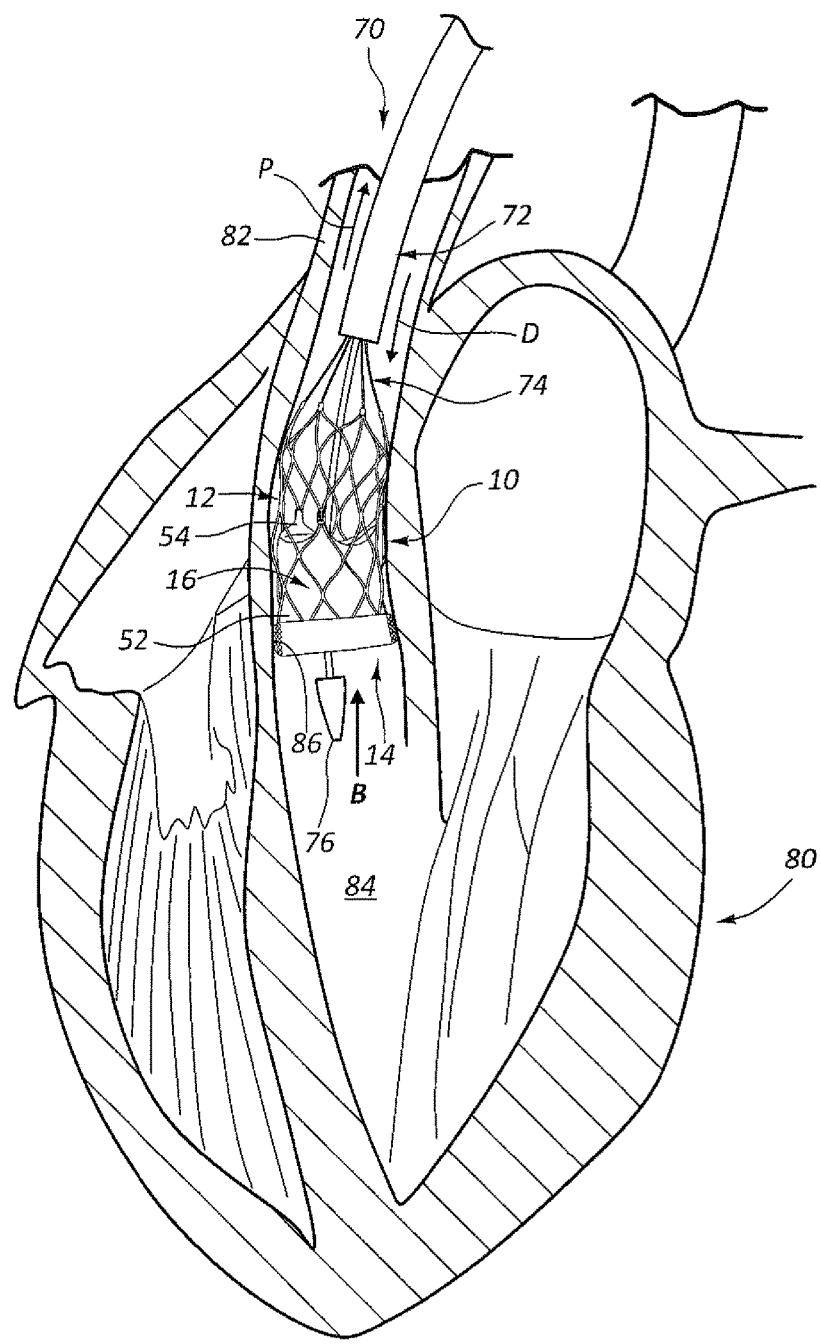
FIG. 15 shows the heart valve assembly and delivery system of FIGS. 9-14 positioned at a native annulus of a heart.

The second orientation has a generally toroid-shaped structure (also referred to as a donut shaped structure), as shown in FIG. 7. The toroid shaped sealing member 14 has interior and exterior surfaces 42, 44, hollow interior 46, and opening 48 (see FIGS. 7 and 8). Free ends are positioned along interior surface 42 (see FIG. 8). Sealing member 14 is connected to stent 12 within opening 48 along interior surface 42 (see FIG. 1). Stent 12 may apply a radially outward directed force to sealing member 14 to compress exterior surface 44 of sealing member 14 against a native annulus. Sealing member 14 may provide an improved seal between heart valve assembly 10 and native annulus 86, as shown in FIG. 15.

Toroid shaped sealing member 14 shown in FIGS. 6-8 includes multiple rolled up layers of wire mesh 40 (e.g., see FIG. 8). At least some of the layers of wire mesh 40 may be arranged in contact with each other. Other layers of wire mesh 40 may be spaced apart with a gap formed there between. The rolled up layers of wire mesh 40 may include at least two layers (e.g., an inner layer positioned adjacent stent 12 and an outer layer arranged to contact the native annulus). Some arrangements of wire mesh 40 when rolled up may include three or more layers, as shown in FIG. 8. The layers of wire mesh 40 may be compressible radially relative to each other to fill gaps between stent 12 and the native annulus when stent 12 compresses sealing member 14 against the native annulus when implanting heart valve assembly 10 at the native annulus. Sealing member 14 may form additional layers of rolled up wire mesh upon compressing sealing member 14. Sealing member 14 may deform as needed to conform to the shape and size of the native annulus. The compressible properties of sealing member 14 when rolled up into the orientation of FIGS. 6-8 may assist in filling irregular shaped voids or gaps between stent 12 and the native annulus that may otherwise result in PVL.

Sealing member 14 may include a shape memory material such as Nitinol. Sealing member 14 may be formed prior to assembly with stent 12 and valve 16. Forming sealing member 14 may include transitioning the generally tubular shape of FIGS. 3 and 4 into the toroid shape of FIGS. 6-8. A plurality of filament strands are braided together to form the tubular shaped wire mesh 40. One end of the tubular shaped wire mesh 40 is rolled over to form the double layer tubular shaped wire mesh 40 shown in FIGS. 3 and 4. Free ends 50 are separated out at proximal end 58 and grouped together to form a plurality of connection points 18. A series of rings may be used to hold sealing member 14 in the rolled up position to form the toroid shape of FIGS. 6-8. A mandrel (not shown) may be inserted into opening 48. The mandrel may have an internal diameter that matches the outer diameter of stent 12. The assembly of sealing member 14 with rings and mandrel may be heat set by placement in an oven set to, for example, about 600° C. until sealing member 14 reaches a heat set temperature of, for example, about 500° C. The heat set temperature may be maintained for a predetermined time period such as, for example, about 1 minute. The toroid shape is fixed in sealing member 14 as the "remembered" or pre-set position. This heat treatment of the shape memory material of sealing member 14 ensures automatic return to the pre-set shape when no external forces are applied (e.g., when in a rest state).

FIGS. 9-14 show heart valve assembly 10 in combination with delivery system 70. Delivery system 70 includes carrier tube 72, deployment member 74, and tip 76 (see FIGS. 10 and 13). Carrier tube 72 may have a maximum outer diameter in the range of, for example, about 10 French (F) to about 25 F, and more particularly in the range of about 16 F to about 20 F.

Figure 9:
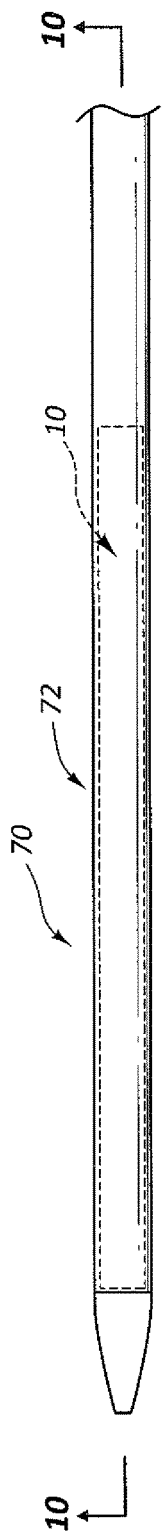
FIG. 9 is a side view of the heart valve assembly of FIG. 1 in use with a delivery system prior to deployment.

FIGS. 9-14 show heart valve assembly 10 at various stages of deployment from delivery system 70. FIGS. 9 and 10 show heart valve assembly 10 completely enclosed in carrier tube 72. FIGS. 11-14 show heart valve assembly 10 either partially deployed (see FIGS. 11-13) or fully deployed (see FIG. 14).

Referring to the cross-sectional view of FIG. 10, heart valve assembly 10 is shown positioned within interior 78 of carrier tube 72 and prepared for delivery to an implantation site. Sealing member 14 is positioned in an unrolled position having a tubular shape (e.g., as shown in FIGS. 3 and 4) and is compressed to fit within carrier tube 72. Sealing member 14 is positioned in series with stent 12 and valve 16, and does not overlap stent 12 and valve 16 within carrier tube 72. Stent 12 and valve 16 are arranged overlapping with valve 16 positioned internally within stent at inflow end portion 20. The series arrangement of sealing member 14 with stent 12 and valve 16, in which sealing member 14 does not overlap valve 16, permits a reduced profile for heart valve assembly 10 within carrier tube 72. A reduced profile for heart valve assembly 10 permits use of a smaller diameter carrier tube 72.

As shown in FIG. 10, outflow end portion 22 of stent 12 is connected to deployment member 74. Deployment member 74 includes a plurality of attachment points connected to individual frame members 26 or pairs of frame members 26 of stent 12. The attachment points of deployment member 74 may be carried by a plurality of elongate arms 75, which have sufficient structural rigidity to transfer tension forces to stent 12 to deploy and re-sheath heart valve assembly 10 (see FIG. 13). Deployment member 74 may include a separate elongate arm 75 for attachment to each free proximal end 28 of stent 12. Elongate arms 75 may be arranged circumferentially relative to each other. Elongate arms 75 may expand and contract in a radial direction during deployment and re-sheathing of heart valve assembly 10.

Tip 76 may extend through heart valve assembly 10 and be positioned at a distal end of carrier tube 72 (see FIG. 10). Tip 76 may have a tapered construction to assist in navigating the delivery apparatus through vessels to the implantation site.

Figure 11:
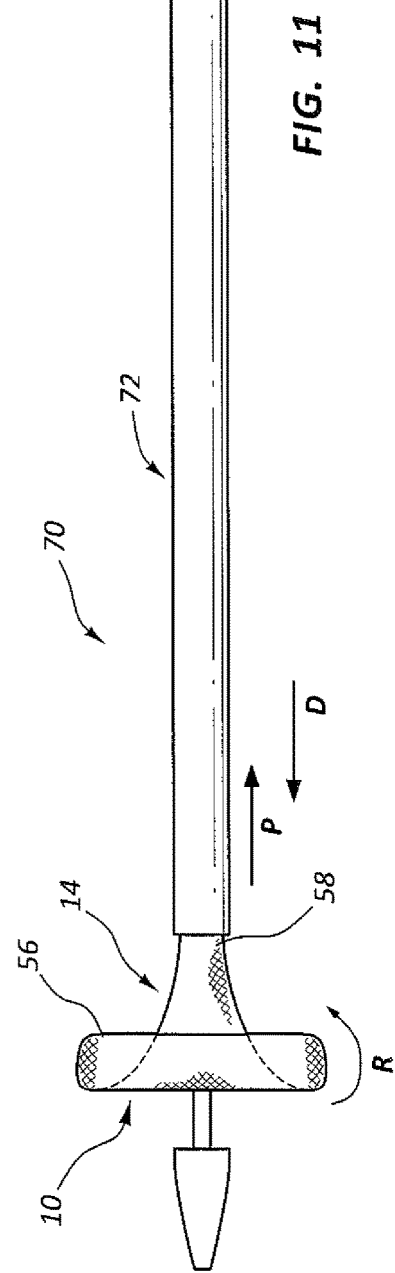

Heart valve assembly 10 is deployed by incrementally withdrawing carrier tube 72 in a proximal direction (away from the heart and toward the operator). Sealing member 14 is first deployed by retracting carrier tube 72 in proximal direction P from a completely advanced position shown in FIGS. 9 and 10 to a first partially retracted position shown in FIG. 11. Sealing member 14 begins to expand radially outward as carrier tube 72 is retracted and distal end 56 of sealing member 14 begins to roll upon itself in direction R, as shown in FIG. 11. Further retracting carrier tube 72 in direction P into the position shown in FIG. 12 allows sealing member 14 to continue to expand and roll upon itself to form a toroid shape. Sealing member 14 automatically positions itself around an exterior surface of stent 12 as sealing member 14 expands and rolls upon itself and inflow end portion 20 of stent 12 is deployed, as shown in FIG. 12.

Further retracting carrier tube 72 in direction P allows stent 12 to continue self-expanding such that outflow end portion 22 is deployed, as shown in FIG. 13. Elongate arms 75 are attached to free proximal ends 28 of stent 12. Sealing member 14 remains positioned at inflow end portion 20. Valve 16 remains positioned within stent 12 and is typically directly connected to stent 12. Valve 16 expands as stent 12 self-expands into the position of FIG. 13.

Any of the positions of heart valve assembly 10 shown in FIGS. 11-13 may be referred to as partially deployed. Heart valve assembly 10 may be partially deployed when at least a portion of stent 12 and sealing member 14 are positioned outside of carrier tube 72 and stent 12 remains connected to deployment member 74. FIG. 14 shows deployment member 74 disconnected from stent 12 so that heart valve assembly 10 is fully deployed. Deployment member 74 may be operated remotely (e.g., at a proximal end of carrier tube 72) to detach from stent 12.

The operator may choose to reposition heart valve assembly 10 relative to a native annulus at an implantation site after partially deploying heart valve assembly 10. Repositioning heart valve assembly 10 typically requires at least partially re-sheathing heart valve assembly 10 within carrier tube 72 to relieve a radially outward force being exerted by heart valve assembly 10 on the native annulus. Relieving the radially outward force permits axial and radial movement of heart valve assembly 10 relative to the native annulus.

Re-sheathing heart valve assembly 10 is initiated by advancing carrier tube 72 in distal direction D (e.g., away from the operator and towards the heart) when the heart valve assembly 10 is at any given partially deployed position. For example, carrier tube 72 may be advanced in distal direction D from the position shown in FIG. 13 until reaching a position shown in any of FIGS. 9-12, or any other axial position relative to heart valve assembly 10 needed to relieve the radially outward force applied to the native annulus. Re-sheathing or partially re-sheathing heart valve assembly 10 may include unrolling sealing member 14 from the rolled up toroid shape shown in FIGS. 12 and 13 to the unrolled or partially unrolled tubular shapes shown in FIGS. 3-5 and 11. Re-sheathing heart valve assembly 10 repositions sealing member 14 aligned axially in series with stent 12.

After re-sheathing heart valve assembly 10 either completely (e.g., the position shown in FIG. 9) or partially (e.g., one of the positions shown in FIGS. 11 and 12), the operator may then reposition heart valve assembly 10 axially and/or radially relative to the native annulus. Heart valve assembly 10 is redeployed at the native annulus by incrementally withdrawing carrier tube 72 in proximal direction P according to the steps shown and described with reference to FIGS. 11-13. If the operator is satisfied with the position of heart valve assembly 10, the operator may detach deployment member 74 from stent 12 to fully deploy heart valve assembly 10, as shown in FIG. 14. Thereafter, the operator may withdraw carrier tube 72, deployment member 74 and tip 76 from heart valve assembly 10 in proximal direction P. Withdrawing tip 76 may include moving tip 76 centrally through an interior of heart valve assembly 10.

FIG. 15 shows heart valve assembly 10 partially deployed within heart 80. Heart 80 is shown in FIG. 15 including aorta 82, left ventricle 84, and native annulus 86. Heart valve assembly 10 is positioned with sealing member 14 aligned with native annulus 86. Stent 12 and valve 16 are positioned within aorta 82. The operator may test for PVL by injecting a contrast agent in the area of heart valve assembly 10. The operator may choose to reposition heart valve assembly 10 to address PVL issues identified using the contrast agent. As described above related to FIGS. 9-13, the operator may at least partially re-sheath heart valve assembly 10 from the partially deployed position shown in FIG. 15 by advancing carrier tube 72 of delivery system 70 in distal direction D. Heart valve assembly 10 is re-sheathed enough to relieve the radially outward force applied by heart valve assembly 10 to native annulus 86. The operator then axially and/or rotationally repositions heart valve assembly 10 relative to native annulus 86. Heart valve assembly 10 is again partially redeployed by retracting carrier tube 72 in proximal direction P. Contrast agent is ejected at native annulus 86 to test for PVL. If needed, the operator may again re-sheath and reposition heart valve assembly 10 relative to native annulus 86. Otherwise, the operator may detach deployment member 74 from stent 12 to completely deploy heart valve assembly 10 at native annulus 86. After detaching stent 12 from deployment member 74, the operator may withdraw carrier tube 72, deployment member 74 and tip 76 from the patient in proximal direction P. Withdrawing tip 76 includes moving tip 76 centrally through an interior of heart valve assembly 10.

With heart valve assembly 10 deployed at native annulus 86, heart valve assembly 10 may operate to control blood flow from left ventricle 84 into aorta 82. Leaflets 54 of valve 16, which are supported by valve cuff 52 (see FIG. 1), may open in response to pressurized flow of blood flow B out of left ventricle 84 and into aorta 82. Leaflets 54 close after the flow of blood from left ventricle 84 stops thereby preventing back flow of blood from aorta 82 into left ventricle 84. Sealing member 14 provides a sealing interface between native annulus 86 and stent 12 and/or valve 16. Sealing member 14 may conform to a shape of native annulus 86 to fill gaps between heart valve assembly 10 and native annulus 86 that limits PVL. Sealing member 14 may have compressible, deformable properties that aid in conforming to the shape of native annulus 86.

Figure 16:
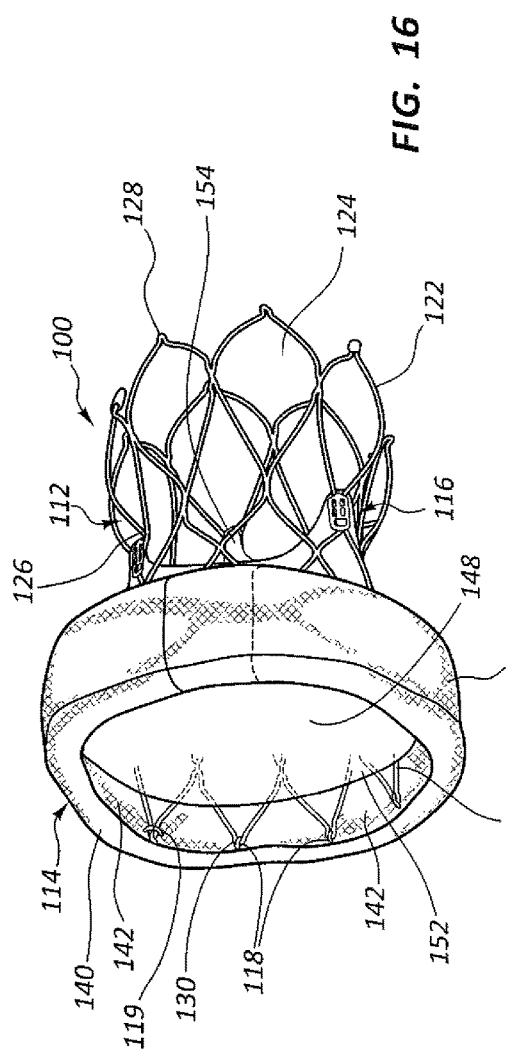
FIG. 16 is a perspective view of another heart valve assembly in accordance with the present disclosure.
Figure 17:
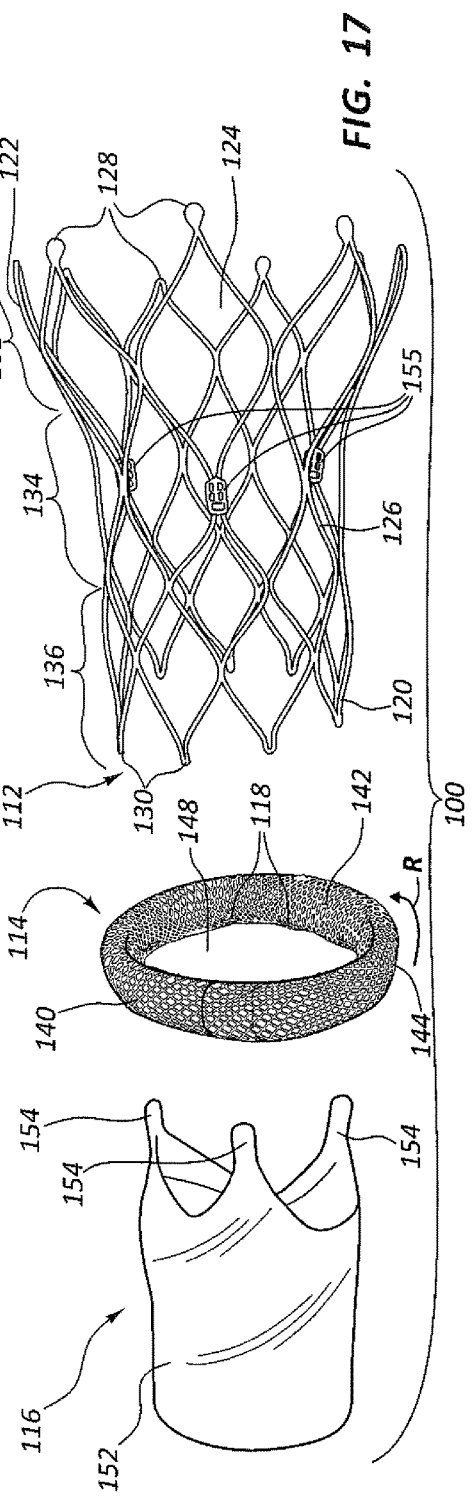
FIG. 17 is an exploded perspective view of the heart valve assembly of FIG. 16.
Figure 20:
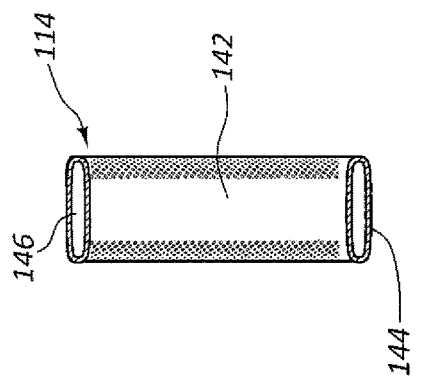
FIG. 20 is a cross-sectional view of the sealing member of FIG. 19 taken along cross-section indicators 20-20.
Figure 19:
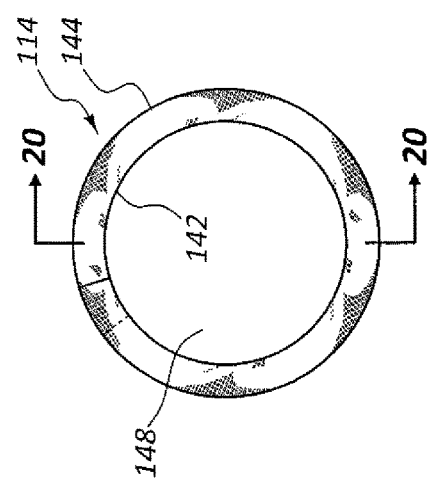
FIG. 19 is an end view of the sealing member of FIG. 18.
Figure 18:
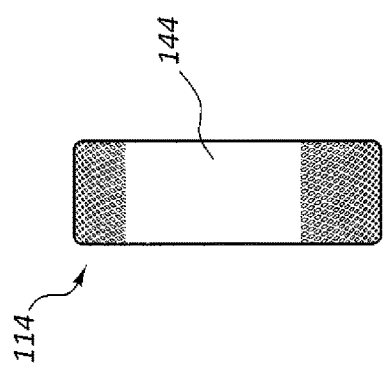
FIG. 18 is a side view of a sealing member of the heart valve assembly of FIG. 16.

Referring now to FIGS. 16-28, another example heart valve assembly 100 in accordance with the present disclosure is shown and described. FIGS. 16 and 17 show heart valve assembly 100 including stent 112, sealing member 114, and valve 116. Stent 112 and valve 116 may have the same or similar construction as stent 12 and valve 16 described above. Stent 112 surrounds and supports valve 116. Valve 116 remains positioned within and is overlapped by stent 112 during delivery and deployment of heart valve assembly 100. Sealing member 114 is connected to stent 112 at a plurality of connection points 118. Connection points 118 may include a fastener or other connecting feature such as a suture. Connection points 118 are positioned along an interior, radially inward facing surface of sealing member 114. Each connection point 118 may gather a plurality of braid pick crossings in material of sealing member 114. Connection points 118 are shown in FIG. 16 as being arranged perpendicular to the circumferential shape of sealing member 114. Connection points 118 may secure a substantial percentage of the interior, radially inward facing surface of sealing member 114 to stent 112, which may provide sealing member 114 the propensity to flip when deployed. All connection points 118 may be arranged in such a perpendicular manner. Alternatively, sealing member 114 may include connection points 119, arranged parallel to the circumferential shape of sealing member 114. (Both parallel connection points 119 and perpendicular connection points 118 are shown in FIG. 16 for disclosure purposes.) In some embodiments, a combination of connection points 118, 119 may be used to connect sealing member 114 to stent 112.

Stent 112 may include inflow and outflow end portions 120, 122, respectively, interior 124, and a plurality of frame members 126 having free proximal and distal ends 128, 130, respectively. Stent 112 includes aortic section 132, sinus section 134, and annulus section 136 (see FIG. 17).

Sealing member 114 includes wire mesh 140. Sealing member 114 may include interior surface 142 (e.g., radially inward facing surface—see FIGS. 19 and 20), exterior surface 144 (e.g., radially outward facing surface—see FIGS. 18-20), hollow interior 146 (see FIG. 20), and opening 148 (see FIGS. 16, 17 and 19). Sealing member 114 may have a generally toroid-shaped construction. Sealing member 114 may have a continuous, unbroken construction circumferentially along interior surface 142 and exterior surface 144 in direction R (see FIG. 17). A shape of sealing member 114 may be referred to as a loop or a continuous loop.

Sealing member 114 may be formed by first constructing a tubular shaped wire mesh (not shown). The length of the tubular shaped wire mesh is at least as long as a circumference of stent 112 along its outer surface at inflow end portion 120. One end of the tubular shaped wire mesh is inserted into an open opposite end of the tubular shaped wire mesh to form a toroid shaped structure. The inserted end is connected to the opposite end using, for example, stitching, welding, or fasteners. The tubular shaped wire mesh may initially have a circular cross-sectional shape. The cross-sectional shape of the tubular shaped wire mesh may be flattened into an elliptical or oval cross-sectional shape prior to or after being formed into the toroid shaped object.

Sealing member 114 may be compressible into a collapsed position during delivery to an implantation site and prior to deployment. Sealing member 114 may automatically expand into the uncompressed, expanded position of FIGS. 16 and 17 when unconstrained. Sealing member 114, unlike sealing member 14 described above, does not unroll into an elongated tubular shaped construction when constrained in a compressed, collapsed position prior to deployment. However, sealing member 114 may flip or invert outward and distally away from stent 112 when moving from the uncompressed, expanded position (see FIG. 16) to a compressed, collapsed position during delivery (see FIG. 22). Sealing member 114 has a toroid shape when in the expanded configuration of FIGS. 16 and 17 with interior surface 142 facing an outer surface of stent 112. Sealing member 114 may flip or invert distally away from stent 112 with interior surface 142 facing radially outward and exterior surface 144 facing radially inward when sealing member is moved toward the compressed, collapsed position.

Sealing member 114 has hollow interior 146 when in the expanded configuration. Sealing member 114 maintains its rolled up shape and hollow interior when collapsed and compressed during delivery. Sealing member 114 may be arranged in series with stent 112 when in the collapsed and compressed configuration during delivery.

Connection points 118 provide a connection between stent 112 and sealing member 114. Connection points 118 may be positioned at any location along interior surface 142. Connection points 118 may be positioned along an edge of interior surface 142, such as adjacent to a distal end of sealing member 114 (see FIG. 16). Connection points 118 may each include, for example, a suture connected to a plurality of individual strands of wire mesh 140 and to distal end 130 of stent 112, as shown in FIG. 16. Connection points 118 may include connection to wire mesh 140 that spans several picks or crossings of the braided strands of wire mesh 140, such as about 5 to about 10 picks. Connection points 118 may include other connection features such as, for example, hooks formed in distal ends 130 of frame members 126, welds, adhesives, or other types of fasteners.

Connection points 118 may concurrently connect sealing member 114 to stent 112 and connect valve 116 to stent 112. Alternatively, sealing member 114 is connected to stent 112 with separate connection features from those connection features (e.g., sutures) used to connect valve 116 to stent 112. In some embodiments, sealing member 114 may be directly connected to valve 116 in addition to being connected to stent 112. Valve 116 may be connected to stent 112 at a plurality of locations separate from connection points 18 used for sealing member 114.

Sealing member 114 may be positioned around an outer peripheral surface of stent 112 when heart valve assembly 100 is deployed. Sealing member 114 may be positioned at annulus section 136 of stent 112 at or near inflow end portion 120. In other arrangements, sealing member 114 may be positioned at other positions along a length of stent 112 such as, for example, along sinus section 134 or aortic section 132. Typically, sealing member 114 is positioned at annulus section 136 such that sealing member 114 is aligned with the native annulus (see FIG. 29).

Connecting stent 112 to sealing member 114 along interior surface 142 positions sealing member 114 around an outer periphery of stent 112 when heart valve assembly 100 is deployed. Deploying sealing member 114 followed by deploying inflow end portion 120 of stent 112 permits sealing member 114 to self-expand at least partially before stent 112 begins to expand (see FIGS. 23-24). This sequential deployment and expansion of sealing member 114 and stent 112 may improve consistency in positioning sealing member 114 around an outer periphery of stent 112 at a subannular location within a native valve annulus. Providing a secure, permanent connection between stent 112 and sealing member 114 may provide improved collapsing of sealing member 114 when being re-sheathed.

Valve 116 is positioned internally within stent 12 when heart valve assembly 10 is assembled, as shown in FIG. 16. Valve 116 may be positioned internally at any location along a length of stent 112. Valve 116 may be connected to stent 112 using, for example, stitching, fasteners, or adhesives. Valve 116 includes cuff 152 and a plurality of leaflets 154 (see FIGS. 16 and 17). Cuff 152 is usually connected to stent 112 using, for example, attachment stitching (not shown). Leaflets 154 may be connected to stent 112 using connectors 155 (see FIG. 17). In the depicted embodiment, three leaflets 154 are shown, although more or less are possible depending on the desired function and location for valve 116. Sealing member 114 may overlap a portion of cuff 152 when heart valve assembly 100 is deployed in the position shown in FIG. 16. Sealing member 114 may be directly connected to cuff 152 as well as stent 112.

FIGS. 21-28 show heart valve assembly 100 in combination with delivery system 170. Delivery system 170 includes carrier tube 172, deployment member 174, and tip 176 (see FIGS. 22 and 27). FIGS. 21-28 show heart valve assembly 100 at various stages of deployment from delivery system 170. FIGS. 21 and 22 show heart valve assembly 100 completely enclosed in carrier tube 172. FIGS. 23-28 show heart valve assembly 100 either partially deployed (see FIGS. 23-27) or fully deployed (see FIG. 28).

FIG. 22 is a cross-sectional view of heart valve assembly 100 and delivery system 170 shown in FIG. 21. Heart valve assembly 100 is positioned within interior 178 of carrier tube 172 and prepared for delivery to an implantation site. Sealing member 114 is positioned in a collapsed position and is compressed to fit within carrier tube 172. Sealing member 114 has an elongate configuration when positioned in carrier tube 172. Sealing member 114 is positioned distal of and in series with stent 112 and valve 116, and does not overlap stent 112 or valve 116 within carrier tube 172. Valve 116 is positioned internal of and overlapping at least inflow end portion 120 of stent 112 during delivery. The series arrangement of sealing member 114 with stent 112 and valve 116, in which sealing member 114 does not overlap valve 116, permits a reduced profile for heart valve assembly 100 within carrier tube 172. A reduced profile for heart valve assembly 100 provides use of a smaller diameter carrier tube 172, which is typically easier to navigate through vessels.

Outflow end portion 122 of stent 112 is connected to deployment member 174. Deployment member 174 includes a plurality of attachment points connected to individual frame members 126 or pairs of frame members 126 of stent 112. The attachment points of deployment member 174 may be carried by a plurality of elongate arms 175, which have sufficient structural rigidity to transfer tensions forces to stent 112 to deploy and re-sheath valve assembly 100 (see FIGS. 22 and 27). Deployment member 174 may include a separate elongate arm 175 for each free proximal end 128 of stent 112 at outlet end portion 122 (see FIGS. 22 and 27). Elongate arms 175 may be arranged circumferentially relative to each other. Elongate arms 175 may expand and contract in a radial direction during deployment and re-sheathing of heart valve assembly 100.

Tip 176 may extend through heart valve assembly 100 and be positioned at an end of carrier tube 172, as shown in FIG. 22. Tip 176 may have a tapered construction to assist in navigating delivery system 170 through vessels to the implantation site.

Heart valve assembly 100 is deployed by incrementally withdrawing carrier tube 172 in a proximal direction. Sealing member 114 is first deployed by retracting carrier tube 172 in proximal direction P from a completely advanced position shown in FIG. 21 to a first partially retracted position shown in FIGS. 23 and 24. Sealing member 114 is oriented with interior surface 142 facing radially outward prior to deployment (see FIG. 22) and during initial retraction of carrier tube 172. Sealing member 114 begins to expand radially outward as carrier tube 172 is retracted. Sealing member 114 also begins to flip in a direction R (see FIGS. 23 and 24) and move toward a position extending around outflow end portion 122 of stent 112. Sealing member 114 may comprise shape memory material that assists in the automatic expansion and flipping of sealing member 114 as carrier tube 172 is retracted.

Figure 26:
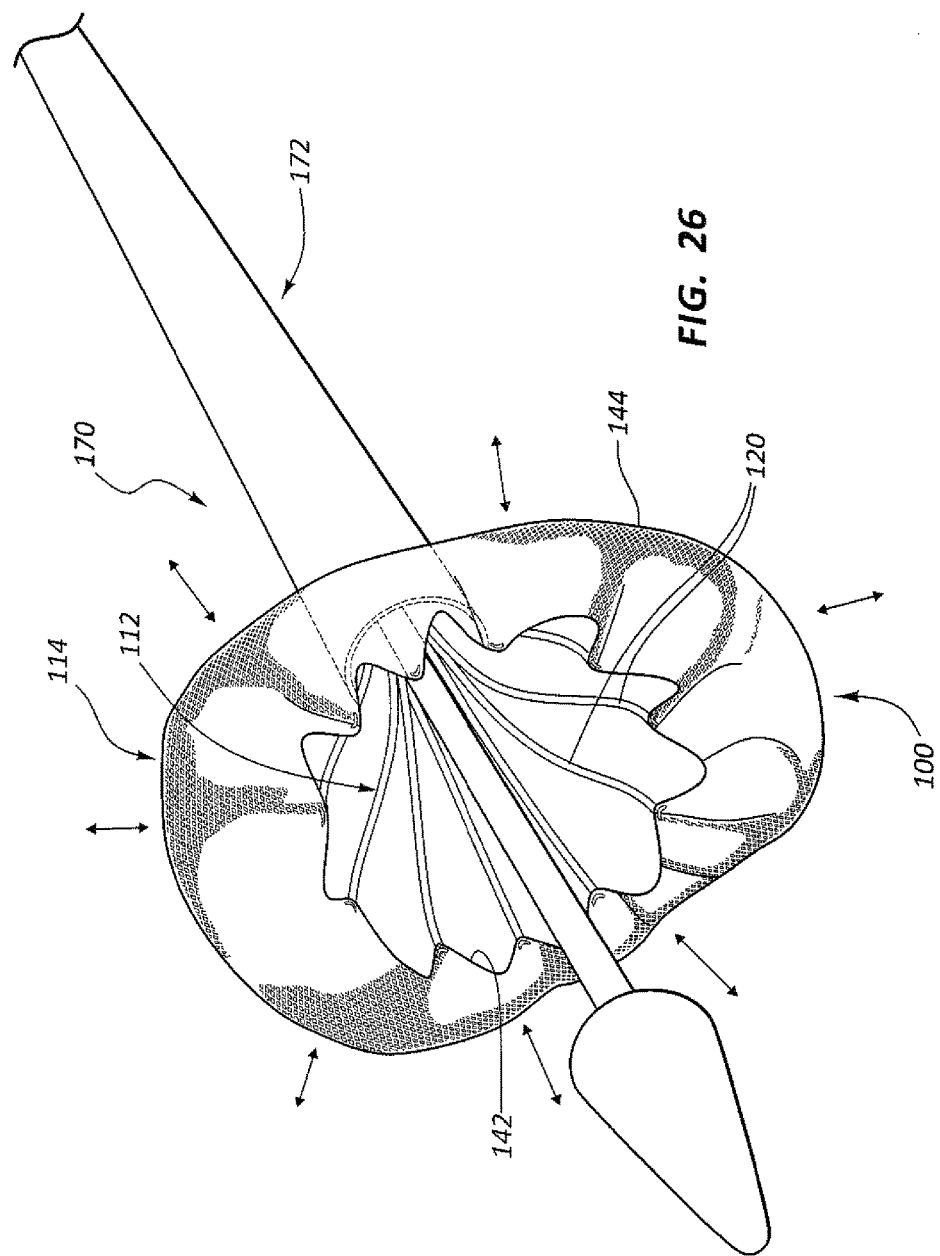
FIG. 26 is a perspective view of the heart valve assembly and delivery system of FIG. 25.

Further retracting carrier tube 172 in direction P from the position shown in FIGS. 23 and 24 into the position shown in FIGS. 25 and 26 allows sealing member 114 to further expand radially outward and to flip or invert into a position overlapping stent 112 and exterior surface 144 facing away from stent 112. FIG. 26 shows sealing member 114 flipped into a position with interior surface 142 facing stent 112. Inflow end portion 120 of stent 112 is exposed outside of carrier tube 172 and also begins to expand radially outward. By deploying sealing member 114 out of carrier tube 172 prior to deploying stent 112, sealing member 114 is able to expand radially outward into a toroid shape while flipping onto and overlapping stent 112 before stent 112 is fully expand radially outward. In other words, the sequential deployment of sealing member 114 from carrier tube 172 followed by deployment of stent 112 permits sealing member 114 to automatically expand and then flip or invert into position around an exterior surface of stent 112 at inflow end portion 120.

Figure 27:
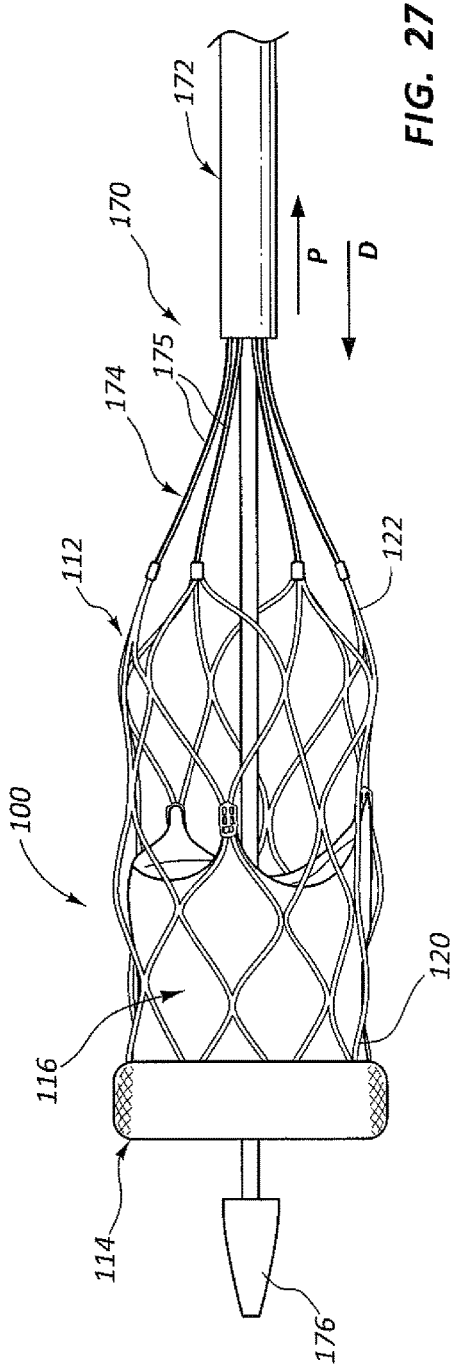
FIG. 27 is a side view of the heart valve assembly of FIG. 25 in a third partially deployed position.

Further retracting carrier tube 172 in direction P allows stent 112 to further self-expand along its length until stent 112 achieves the expanded position shown in FIG. 27. In other words, outflow end portion 122 of stent 112 is deployed from carrier tube 172, but still remains connected to deployment member 174. Sealing member 114 remains positioned at inflow end portion 120. Valve 116 is typically connected to and supported internally within stent 112, which causes valve 116 to expand as stent 112 self-expands upon withdrawal of carrier tube 172.

Figure 28:
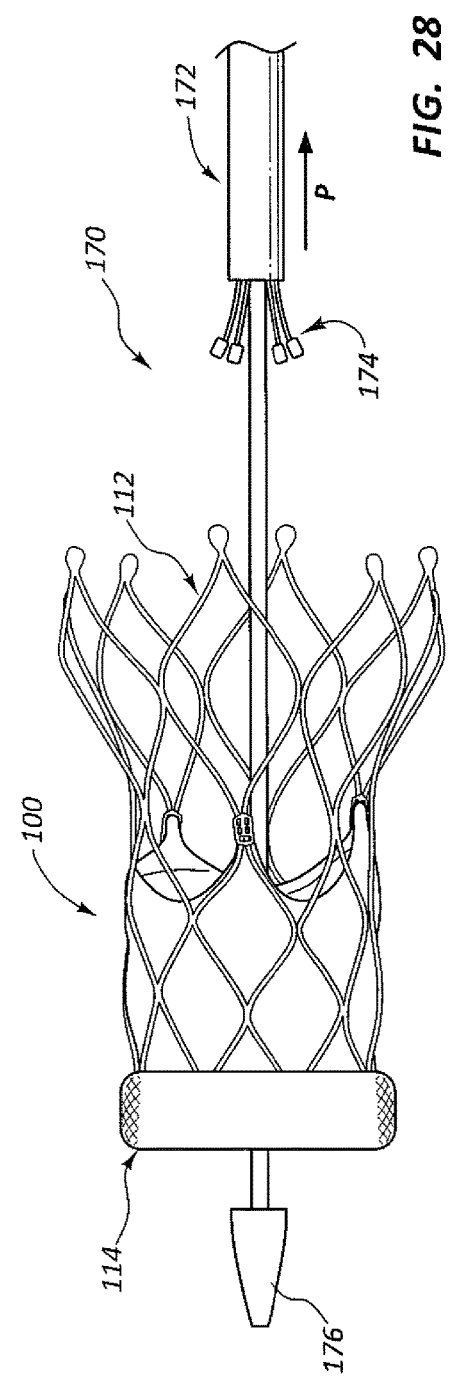
FIG. 28 is a side view of the heart valve assembly of FIG. 27 in a fully deployed position.

Any of the positions of heart valve assembly 100 shown in FIGS. 23-27 may be referred to as partially deployed. Heart valve assembly 100 may be partially deployed when at least a portion of stent 112 and/or sealing member 114 is positioned outside of carrier tube 172 and stent 112 remains connected to deployment member 174. FIG. 28 shows deployment member 174 disconnected from stent 112 so that heart valve assembly 100 is fully deployed. Deployment member 174 may be operated remotely (e.g., at a proximal end of carrier tube 172) to detach from stent 112.

The operator may choose to reposition heart valve assembly 100 relative to a native annulus at an implantation site after partially deploying heart valve assembly 100. Repositioning heart valve assembly 100 typically requires re-sheathing of heart valve assembly 100 within carrier tube 172 to relieve a radially outward force being exerted by heart valve assembly 100 on the native annulus. Relieving the radially outward force permits axial and radial movement of heart valve assembly 100 relative to the native annulus.

Re-sheathing heart valve assembly 100 is initiated by advancing carrier tube 172 in distal direction D (e.g., away from the operator and toward the heart) when heart valve assembly 100 is at any given partially deployed position. For example, carrier tube 172 may be advanced in distal direction D from the position shown in FIG. 27 until reaching a position shown in any of FIGS. 21-26, or any other axial position relative to heart valve assembly 100 needed to relieve the radially outward force applied to the native annulus. Re-sheathing heart valve assembly 100 repositions sealing member 114 aligned axially in series with stent 112.

After re-sheathing heart valve assembly 100 either completely (e.g., the position shown in FIG. 21) or partially (e.g., one of the positions shown in FIGS. 23-27), the operator may then reposition heart valve assembly 100 axially and/or radially relative to the native annulus. Heart valve assembly 100 is redeployed at the native annulus by incrementally withdrawing carrier tube 172 in proximal direction P according to the steps shown and described with reference to FIGS. 21-27. If the operator is satisfied with the position of heart valve assembly 100, the operator may detach deployment member 174 from stent 112 to fully deploy heart valve assembly 100, as shown in FIG. 28. Thereafter, the operator may withdraw deployment member 174 and tip 176 from heart valve assembly 100 in proximal direction P. Withdrawing tip 176 includes moving tip 176 centrally through an interior of heart valve assembly 100.

Figure 29:
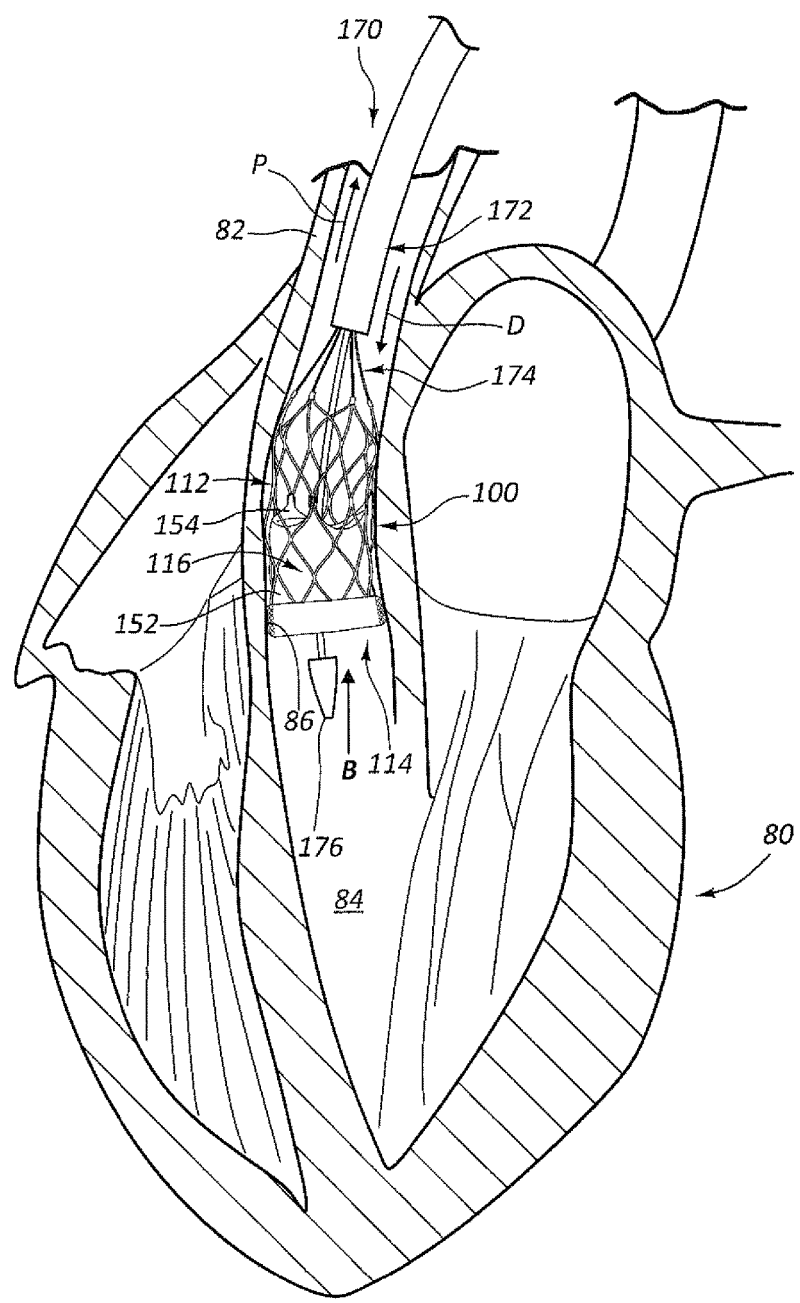
FIG. 29 shows the heart valve assembly and delivery system of FIGS. 21-28 positioned at a native annulus of a heart.

FIG. 29 shows heart valve assembly 100 partially deployed within heart 80. Heart valve assembly 100 is positioned with sealing member 114 aligned with native annulus 86. Stent 112 and valve 116 are positioned within aorta 82. The operator may test for PVL by injecting a contrast agent in the area of heart valve assembly 100. The operator may choose to reposition heart valve assembly 100 to address PVL issues identified using the contrast agent. As described above related to FIGS. 21-27, the operator may at least partially re-sheath heart valve assembly 100 from the partially deployed position shown in FIG. 29 by advancing carrier tube 172 of delivery system 170 in distal direction D. Heart valve assembly 100 is re-sheathed enough to relieve the radially outward force applied by heart valve assembly 100 to native annulus 86. The operator then axially and/or rotationally repositions heart valve assembly 100 relative to native annulus 86. Heart valve assembly 100 is again partially redeployed by retracting carrier tube 172 in proximal direction P. Contrast agent is ejected at native annulus 86 to test for PVL. If needed, the operator may again re-sheath and reposition heart valve assembly 100 relative to native annulus 86. Otherwise, the operator may detach deployment member 174 from stent 112 to completely deploy heart valve assembly 100 at native annulus 86. Carrier tube 172, deployment member 174, and tip 176 may then be withdrawn from the patient.

With heart valve assembly 100 deployed at native annulus 86, heart valve assembly 100 may operate to control blood flow between left ventricle 84 into aorta 82. Leaflets 154 of valve 116, which are supported by valve cuff 152, may open in response to pressurized flow of blood out of left ventricle 84 and into aorta 82. Leaflets 154 close after the flow of blood flow B from left ventricle 84 stops thereby preventing back flow of blood from aorta 82 into left ventricle 84. Sealing member 114 provides a sealing interface between native annulus 86 and stent 112 and/or valve 116. Sealing member 114 may conform to a shape of native annulus 86 to fill gaps between heart valve assembly 100 and native annulus 86 that limits PVL. Sealing member 114 may have compressible, deformable properties that aid in conforming to the shape of native annulus 86.

A heart valve assembly in accordance with the present disclosure includes a heart valve, a self-expandable and collapsible stent, and a sealing member. The stent includes an inflow end and an outflow end, and surrounds and supports the heart valve. The sealing member is connected to the inflow end of the stent and extends around a periphery of the stent. The sealing member is connected to the inflow end of the stent, overlaps a portion of the heart valve, and extends around an outer periphery of the stent.

The sealing member may assume an elongated hollow tubular shape when collapsed and constrained. The sealing member may comprise a braided wire mesh. A plurality of wires of the braided wire mesh may be connected to the stent at a single connection point. The sealing member may include a plurality of wires braided to form a mesh, and at least some of the plurality of wires are connected to the stent. The stent may include a plurality of strut members, and the sealing member is connected to distal free ends of the plurality of strut members. The sealing member may be connected to the stent with a plurality of fasteners at spaced apart locations around a circumference of the sealing member. The sealing member may be connected to the stent with a plurality of weld connections. The stent and sealing member may be movable from collapsed positions to expanded positions, and movable from expanded positions to collapsed positions. The heart valve assembly may further include a plurality of marker bands positioned at connection points between the stent and the sealing member. The sealing member rolls up into a pre-formed toroid shape when unconstrained.

Another aspect of the present disclosure relates to a heart valve assembly that includes a heart valve, a self-expandable and collapsible stent, and a sealing member. The stent includes an inflow end and an outflow end, and surrounds and supports the heart valve. The sealing member includes a wire mesh having a hollow toroid shape with a central opening and an inward facing surface when in an expanded configuration. The sealing member is collapsible into an elongated configuration for delivery through a vessel. The stent extends into the central opening and is connected to the inward facing surface at a plurality of connection points when in the expanded configuration.

The sealing member may have an elongated tubular shape having first and second ends when in a collapsed, constrained configuration. The first end may be connected to the stent and the second end may be configured to automatically roll upon itself when the sealing member moves between the collapsed and expanded configurations. The radially inward facing surface may face radially outward when the sealing member is collapsed into the elongated configuration. The wire mesh may include a plurality of braided wire strands intersecting at a plurality of pick points, and the stent is connected to the wire mesh at some of the plurality of the pick points. The sealing member may invert when moving between the expanded configuration and the elongated configuration. The sealing member may be connected to the stent with a suture connection.

A further aspect of the present disclosure relates to a method of manufacturing a heart valve assembly. The method may include providing a stent and a sealing member that each have a self-expandable and collapsible construction. The stent includes an inflow end and an outflow end and is configured to support a heart valve internally. The method includes positioning the sealing member around an outer periphery of the stent at the inflow end, and connecting the stent to the sealing member at a plurality of connection points.

Connecting the stent to the sealing member may include securing with at least one of a suture and a clip. The sealing member may include a wire mesh formed from a plurality of braided wire members, and the method may further include separating out at least some of the plurality of braided wire members and grouping together the separated out wire members to form the plurality of connection points.

Another method in accordance with the present disclosure relates to a method of deploying a heart valve assembly at an annulus. The method includes providing the valve assembly including a stent surrounding a valve member and a sealing member connected to the stent, and collapsing the valve assembly such that the sealing member and stent are in series.

The method may further include positioning the valve assembly within a carrier tube, positioning the carrier tube at the annulus, retracting the carrier tube to expose the heart valve assembly with the sealing member positioned at the annulus, wherein the sealing member transitions from a collapsed position into an expanded position, and forming a seal between the annulus and the stent with the sealing member to limit paravalvular leaking. The sealing member may extend around an outer peripheral surface of the stent in the expanded position. The annulus may include a native aortic valve. The method may include retracting the valve assembly into the carrier tube after advancing the heart valve assembly out of the carrier tube. The method may include providing a delivery assembly configured to move the valve assembly relative to the carrier tube and disconnecting the valve assembly from the delivery assembly after forming the seal.

Forming the sealing member into a toroid shape may include rolling a tubular-shaped piece of wire mesh upon itself about an axis that extends circumferentially around the tubular shaped mesh material. Once the mesh material is rolled up to form the toroid shape, the wire mesh may be heat set. The sealing member may be unrolled for purposes of, for example, being collapsed and held within a carrier tube for delivery of the heart valve assembly to an implantation site. One end of the sealing member may be connected to the stent. Upon being released from the carrier tube, the sealing member may transition from a collapsed position into an expanded position by rolling upon itself until attaining the heat set position. The sealing member may be arranged extending around an outer periphery of the stent when in the expanded position.

As used in this specification and the appended claims, the term "engage" and "engagable" are also used broadly to mean interlock, mesh, or contact between two devices. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising." The term "distal" refers to the end of the heart valve assembly closest to the heart and a direction away from the operator, and the term "proximal" refers to the end of the heart valve assembly farthest from the heart and a direction toward the operator. The term "inlet end" refers to an end of the heart valve assembly closest to an outlet opening of the heart and which receives blood flow from the heart. An "outlet end" of the heart valve assembly refers to that portion of the heart valve assembly through which blood flows out of the heart valve assembly in a direction away from the heart.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A heart valve assembly system, comprising:
a heart valve assembly comprising:
- a heart valve;
- a self-expandable and collapsible stent surrounding and supporting the heart valve, the stent comprising a plurality of strut members and defining an inflow end and an outflow end, the plurality of strut members including free ends at the inflow end of the stent; and
- a sealing member connected to the inflow end of the stent and overlapping a portion of the heart valve when the heart valve assembly is in an unconstrained condition, the sealing member extending around an outer periphery of the stent when the heart valve assembly is in the unconstrained condition, the sealing member formed of a braided wire mesh having a plurality of wires,
- wherein individual ones of the plurality of wires each include a free end, and the plurality of free ends are connected together at connection points in a plurality of bunches, the connection points spaced apart from one another and directly connected to the free ends of the strut members; and a delivery device comprising:
- a carrier tube adapted to receive the heart valve assembly therein in a constrained condition.

2. The heart valve assembly system of claim 1, wherein the sealing member assumes an elongated hollow tubular shape when the heart valve assembly is in the unconstrained condition.

3. The heart valve assembly system of claim 1, wherein the sealing member is connected to the stent with a plurality of fasteners at spaced apart locations around a circumference of the sealing member.

4. The heart valve assembly system of claim 1, wherein the sealing member is connected to the stent with a plurality of fasteners.

5. The heart valve assembly system of claim 1, wherein the stent and sealing member are movable from collapsed positions to expanded positions, and movable from expanded positions to collapsed positions.

6. The heart valve assembly system of claim 1, further comprising:
a plurality of marker bands positioned at the connection points between the stent and the sealing member.

7. The heart valve assembly system of claim 1, wherein the sealing member rolls up into a pre-formed toroid shape when the heart valve assembly is in the unconstrained condition.

8. The heart valve assembly system of claim 1, wherein the plurality of bunches has a total number equal to a total number of the plurality of free ends of the strut members at the inflow end of the stent.

9. The heart valve assembly system of claim 1, wherein each bunch of the plurality of bunches includes an equal number of free ends of the plurality of wires.

10. The heart valve assembly system of claim 9, wherein the number of free ends in each bunch is equal to a total number the plurality of wires forming the sealing member divided by a total number of the connection points.

11. The heart valve assembly system of claim 1, wherein the delivery device further comprises when the heart valve assembly is received within the carrier tube.

12. The heart valve assembly system of claim 11, wherein each attachment point is connected to a pair of struts when the heart valve assembly is received within the carrier tube.

13. The heart valve assembly system of claim 11, wherein each attachment point is connected to an individual strut when the heart valve assembly is received within the carrier tube.

14. The heart valve assembly system of claim 11, wherein the attachment points of the deployment member are carried by elongate arms.

* * * * *